United States Patent
Vollmers

(10) Patent No.: US 8,124,080 B2
(45) Date of Patent: *Feb. 28, 2012

(54) HUMAN MONOCLONAL ANTIBODY HAVING FAT-REDUCING EFFECT

(75) Inventor: Heinz Peter Vollmers, Wurzburg (DE)

(73) Assignee: Patrys Limited, Melbourne, Victoria (AU)

( * ) Notice: Subject to any disclaimer, the term of this patent is extended or adjusted under 35 U.S.C. 154(b) by 883 days.

This patent is subject to a terminal disclaimer.

(21) Appl. No.: 10/578,856

(22) PCT Filed: Nov. 12, 2004

(86) PCT No.: PCT/DE2004/002503
§ 371 (c)(1),
(2), (4) Date: Jul. 18, 2006

(87) PCT Pub. No.: WO2005/049635
PCT Pub. Date: Jun. 2, 2005

(65) Prior Publication Data
US 2008/0045701 A1 Feb. 21, 2008

(30) Foreign Application Priority Data
Nov. 14, 2003 (DE) .................. 103 53 175

(51) Int. Cl.
C07K 14/00 (2006.01)
C07K 16/18 (2006.01)
C12P 21/00 (2006.01)

(52) U.S. Cl. .................. 424/133.1; 530/388.1; 530/350; 530/387.1; 436/548

(58) Field of Classification Search ............... 424/133.1; 530/388.1, 350, 387.1; 436/548
See application file for complete search history.

(56) References Cited

U.S. PATENT DOCUMENTS

| | | |
|---|---|---|
| 5,610,280 A | 3/1997 | Brandt et al. |
| 5,639,641 A | 6/1997 | Pedersen et al. |
| 5,639,863 A | 6/1997 | Dan |
| 5,763,224 A | 6/1998 | Caras et al. |
| 6,677,442 B1 | 1/2004 | Wang et al. |
| 6,995,240 B1 | 2/2006 | Panayi et al. |
| 7,049,132 B1 | 5/2006 | Lee |
| 7,468,183 B2 | 12/2008 | Nilsson et al. |
| 7,521,046 B2 | 4/2009 | Nilsson et al. |
| 7,785,589 B2 | 8/2010 | Nilsson et al. |
| 2004/0048243 A1 | 3/2004 | Arap et al. |
| 2005/0123571 A1 | 6/2005 | Rossini et al. |
| 2005/0191294 A1 | 9/2005 | Arap et al. |
| 2006/0239968 A1 | 10/2006 | Arap et al. |
| 2008/0003200 A1 | 1/2008 | Arap et al. |
| 2008/0108133 A1* | 5/2008 | Vollmers et al. ............ 435/330 |

FOREIGN PATENT DOCUMENTS

| | | |
|---|---|---|
| DE | 41 07 154 A1 | 4/1992 |
| DE | 692 12 671 T2 | 3/1997 |
| DE | 692 29 110 T2 | 11/1999 |
| DE | 695 27 975 T2 | 3/2003 |
| DE | 102 30 516 A1 | 1/2004 |
| EP | 1 106 183 A2 | 6/2001 |
| EP | 1 141 019 B1 | 4/2004 |
| WO | 97/02479 | 1/1997 |
| WO | 97/13844 A1 | 4/1997 |
| WO | 99/28461 | 6/1999 |
| WO | 99/53051 | 10/1999 |
| WO | 99/65935 A2 | 12/1999 |
| WO | 00/12562 | 3/2000 |
| WO | 00/37489 A2 | 6/2000 |
| WO | 00/37489 A3 | 6/2000 |
| WO | WO 00/56772 A1 | 9/2000 |
| WO | 01/62932 A1 | 8/2001 |
| WO | 01/83560 A1 | 11/2001 |
| WO | 02/02641 A1 | 1/2002 |
| WO | 02/12502 A2 | 2/2002 |
| WO | WO 0212502 * | 2/2002 |
| WO | 02/084277 A1 | 10/2002 |
| WO | 03/011907 A3 | 2/2003 |
| WO | WO 03/048321 A2 | 6/2003 |
| WO | 03/076472 A2 | 9/2003 |
| WO | 03/076472 A3 | 9/2003 |
| WO | WO 03/084477 A2 | 10/2003 |
| WO | 2004/005351 A2 | 1/2004 |
| WO | 2004/020999 A1 | 3/2004 |
| WO | 2004/081027 A2 | 9/2004 |
| WO | 2004/081027 A3 | 9/2004 |
| WO | 2005/001052 A2 | 1/2005 |
| WO | 2005/045428 A2 | 5/2005 |
| WO | 2005/047332 A1 | 5/2005 |
| WO | 2005/047332 A1 | 5/2005 |
| WO | 2005/065418 A2 | 7/2005 |
| WO | 2005/085862 A1 | 9/2005 |
| WO | 2005/092922 A2 | 10/2005 |
| WO | 2005/092922 A3 | 10/2005 |
| WO | 2005/094159 A2 | 10/2005 |
| WO | WO 2010/088739 A1 | 8/2010 |

OTHER PUBLICATIONS

MacCallum et al. (J. Mol. Biol. 262:732-745 (1996)).*
de Pascalis et al. (Journal of Immunology 169, 3076-3084 (2002)).*
Casset et al. (BBRC 307, 198-205, (2003)).*
Vajdos et al. (J. Mol. Biol. 320, 415-428 (2002)).*

(Continued)

*Primary Examiner* — Lynn Bristol
(74) *Attorney, Agent, or Firm* — Pillsbury Winthrop Shaw Pittman LLP

(57) ABSTRACT

A purified polypeptide having an amino acid sequence that is substantial identical with the amino acid sequence of SEQ ID NO:1, SEQ ID NO:3, or both, in which the polypeptide binds low density lipoproteins (LDL) or oxidized LDL (oxLDL), or both, and particularly binds well to LDL cholesterol and oxidized LDL cholesterol. The polypeptide may be used in combination with conventional adjuvants or carrier substances for producing a drug having a fat-reducing effect and for producing drugs for aiding in the treatment of renal diseases.

27 Claims, 7 Drawing Sheets

OTHER PUBLICATIONS

Holm et al (Mol. Immunol. 44: 1075-1084 (2007)).*
Chen et al. (J. Mol. Bio. 293, 865-881 (1999)).*
Wu et al. (J. Mol. Biol. 294, 151-162 (1999)).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Teerlink et al. (J. Lipid Res. 45:954-966 (2004)).*
McNamara et al (J. Lipid Res. 37:1924-1935 (1996)).*
Dufner (Trends Biotechnol. 24(11):523-29 (2006)).*
Berger, C.L., et al., A Lymphocyte Cell Surface Heat Shock Protein Homologous to the Endoplasmic Reticulum Chaperone, Immunoglobulin Heavy Chain Binding Protein BIP, Int. J. Cancer, 71:1077-1085 (1997).
Bjorge et al., Complement-Regulatory Proteins in Ovarian Malignancies, Int. J. Cancer, 70:14-25 (1997).
Brandlein et al., "Natural IgM Antibodies and Immunosurveillance Mechanisms Against Epithelial Cancer Cells in Humans," Cancer Research, 63: 7995-8005, Nov. 15, 2003.
Brändlein et al., Characterization of Five New Fully Human Monoclonal IgM Antibodies Isolated from Carcinoma Patients, Proceedings of the Annual Meeting of the American Association for Cancer Research 43:970, Mar. 2002 (Abstract).
Brändlein et al., Human Monoclonal IgM Antibodies with Apoptotic Activity isolated from Cancer Patients, Human Antibodies 11:107-119, 2002.
Brändlein, S., et al., CFR-1 Receptor as Target for Tumor-specific Apoptosis Induced by the Natural Human Monoclonal Antibody PAM-1, Oncology Reports, 11:777-784 (2004).
Brändlein, S., et al., Cysteine-rich Fibroblast Growth Factor Receptor 1, a New Marker for Precancerous Epithelial Lesions Defined by the Human Monoclonal Antibody PAM-1, Cancer Research, 63:2052-2061 (2003).
Brändlein, S., et al., PAM-1, a Natural Human IgM Antibody as New Tool for Detection of Breast and Prostate Precursors, Human Antibodies, 13:97-104 (2004).
Chen, G., et al., Protein Profiles Associated With Survival in Lung Adenocarcinoma, www.pnas.org/cgi/doi/10.1073/pnas.2233850100 pp. 1-6 (2003).
Database entry AAB02178 dated Jun. 11, 1996.
Faller et al., HAB-1, a New Heteromyeloma for Continuous Production of Human Monoclonal Antibodies, Br. J. Cancer 62:595-598 (1990).
Gonatas et al., MG-160, A Membrane Sialoglycoprotein of the Medial Cisternae of the Rat Golgi Apparatus, Binds Basic Fibroblast Growth Factor and Exhibits a High level of Sequence Identity to a Chicken Fibroblast Growth Factor Receptor, J. Cell Science 108:457-467, 1995.
Grossman, H.B., Natural Antibody to a Human Bladder Carcinoma Cell Line, Cancer Immunol. Immunother. 13:89-92 (1982).
Hensel et al., A New Variant of Cystein-Rich FGF Receptor (CFR-1) Specifically Expressed on Tumor Cells, Proceedings of the American Association for Cancer Research 41:698 (abstract 4438), Mar. 2000.
Hensel et al., A Novel Proliferation-associated Variant of CFR-1 Defined by a Human Monoclonal Antibody, Laboratory Investigation 81:1097-1108, 2001.
Hensel et al., Characterization of Glycosylphosphatidylinositol-linked Molecule CD55/Decay-accelerating Factor as the Receptor for Antibody SC-1-induced Apoptosis, Cancer Research 59:5299-5306, 1999.
Hensel et al., Mitogenic Autoantibodies in *Helicobacter pylori*-Associated Stomach Cancerogenesis, International Journal of Cancer 81:229-235, 1999.
Hensel, F., et al., "Regulation of the new coexpressed CD55 (decay-accelerating factor) receptor on stomach carcinoma cells involved in antibody SC-1-induced apoptosis", Laboratory Investigation, 81(11):1553-1563 (2001).
Huang et al., Sulindac Sulfide-induced Apoptosis Involves Death Receptor 5 and the Caspase 8-dependent Pathway in Human Colon and Prostate Cancer Cells, Cancer Research 61:6918-6924 (2001).
Iwadate, Y., et al., Molecular Classification and Survival Prediction in Human Gliomas Based on Proteome Analysis, Cancer Research, 64:2496-2501 (2004).
Jamora, C., et al., Inhibition of Tumor Progression by Suppression of Stress Protein GRP78/BiP Induction in Fibrosarcoma B/C10ME, Proc. Natl. Acad. Sci. USA, 93:7690-7694 (1996).
Jansson, et al., The Human Repertoire of Antibody Specificities Against Thomsen-Friedenreich and TN-carcinoma-associated antigens as defined by Monoclonal Antibodies, Cancer Immunology 34:294-298, 1992.
Kamitani, H., et al., Expression of 15-Lipoxygenase by Human Colerectal Carcinoma Caco-2 Cells During Apoptosis and Cell Differentiation, The Journal of Biological Chemistry, 273(34):21569-21577 (1998).
Lee, A.S., Mammalian Stress Response: Induction of the Glucose-Regulated Protein Family, Current Opinion in Cell Biology, 4:267-273 (1992).
Little, E., et al., The Glucose-Regulated Proteins (GRP78 and GRP94): Functions, Gene Regulation, and Applications, Critical Reviews In Eukaryotic Gene Expression, 4(1):1-18 (1994).
Liu et al., Towards Proteome-Wide Production of Monoclonal Antibody by Phage Display, J. Mol. Bio. 315:1063-1073 (2002).
Mammalian Gene Collection (MGC) Program Team, "Generation and Initial Analysis of more than 15,000 Full-Length Human and Mouse cDNA Sequences" PNAS USA 99:16,899-16,903 (2002).
Masatoshi, K., Antibody CDNA, Abstract JP Publication No. 09098786 0, Apr. 15, 1997.
Mintz, P.J., et al., Fingerprinting the Circulating Repertoire of Antibodies from Cancer Patients, Nature Biotechnology, 21:57-63 (2003).
Misra, U.K., et al., The Role of Grp 78 in $\alpha_2$-Macroglubulin-Induced Signal Transduction, The Journal of Biological Chemistry, 277(44):42082-42087 (2002).
Mourelatos et al., Cloning and Sequence Analysis of the Human MG160, a Fibroblast Growth Factor and E-Selectin Binding Membrane Sialoglycoprotein of the Golgi Apparatus, DNA Cell Biol. 12:1121-1128 (1996).
Myung, J-K, et al., Expressional Patterns of Chaperones in Ten Human Tumor Cell Lines, Proteome Science, 2:8:1-21 (2004).
Pfaff, M., et al., Human Monoclonal Antibody Against a Tissue Polypeptide Antigen-related Protein from a Patient with a Signet-Ring Cell Carcinoma of the Stomach, Cancer Research, 50:5192-5198 (1990).
Pohle et al., Lipoptosis: Tumor Specific Cell Death by Antibody-Induced Intracellular Lipid Accumulation, Cancer Research, 64:11, 3900-3906 (2004).
Sato, K., et al., Immunotherapy Using Heat-Shock Protein Preparations of Leukemia Cells After Syngenic Bone Marrow Transplantation in Mice, Blood, 98(6):1852-1857 (2001).
Sugawara, S., et al., Suppression of Stress Protein GRP78 Induction in Tumor B/C10ME Eliminates Resistance to Cell Mediated Cytotoxicity, Cancer Research, 53:6001-6005 (1993).
Timmermann W., et al., Immuntherapie: ein Antikörper gegen Magenkrebs Blick Jan. 1999, Artikel 6, internet page http://www.uni-wuerzburg.de/blick1999-1/991do6-t.html.
Vollmers et al., "Apoptosis of Stomach Carcinoma Cells Induced by a Human Monoclonal Antibody," Cancer 76:550-558 (1995).
Vollmers et al., "Human Monoclonal Antibodies from Stomach Carcinoma Patients React with *Helicobacter pylori* and Stimulate Stomach Cells in vitro," Cancer 74:1525-1532, 1994.

Vollmers et al., "SC-1, a Functional Human Monoclonal Antibody against Autologous Stomach Carcinoma Cells," Cancer Res. 49:2471-2476, 1989.

Vollmers et al., Adjuvant Therapy for Gastric Adenocarcinoma with the Apoptosis-Inducing Human Monoclonal Antibody SC-1: First Clinical and Histopathological Results, Oncology Reports 5:549-552 (1998).

Vollmers, H.P., et al., Monoclonal Antibodies NORM-1 and NORM-2 Induce More Normal Behavior of Tumor Cells In Vitro and Reduce Tumor Growth In Vivo, Cell, 40:547-557 (1985).

Vollmers, P., et al., Tumor-Specific Apoptosis Induced by the Human Monoclonal Antibody SC-1: A New Therapeutical Approach for Stomach Cancer, Oncology Reports, 5:35-40 (1998).

Wixler et al., "Identification of Novel Interaction Partners for the conserved membrane proximal region of alpha-integrin cytoplasmic domains," FEBS Letters vol. 445, Feb. 26, 1999.

Arap, M.A., et al., Cell Surface Expression of the Stress Response Chaperone GRP78 Enables Tumor Targeting by Circulating Ligands, *Cancer Cell*, 2004, 6:275-284.

Mueller-Hermelink, et al., U.S. Appl. No. 10/579,290, "Adenocarcinoma Specific Antibody SAM-6, and Uses Thereof", May 15, 2006.

Vollmers, Heinz Peter, U.S. Appl. No. 11/945,916, "Novel Glycosylated Peptide Target in Neoplastic Cells", Nov. 27, 2007.

U.S. Appl. No. 12/702,974, filed Feb. 2010, Ilag.

* cited by examiner

HUMAN MONOCLONAL ANTIBODY HAVING FAT-REDUCING EFFECT

This application is a U.S. national phase of International application no.
PCT/DE2004/002503, filed Nov. 12, 2004, and claims the benefit of priority of German application no. 103 53 175.0, filed Nov. 14, 2003.

The invention relates to a purified polypeptide (SAM-6.10) and its use in combination with conventional adjuvants and/or carrier substances for producing a drug having a fat-reducing effect and for producing a drug for treating renal diseases.

BACKGROUND OF THE INVENTION

Excessive cholesterol (hyperlipoproteinemia) in the body leads to sclerosis (arteriosclerotic plaque) of the interior layers of the blood vessels, and to a gradual hardening and thickening of the arterial walls. In an extreme case, it threatens blocking of the vessels, or in the event of rupture of the plaque, thrombus formation. Arteriosclerosis with its secondary illnesses (coronary illnesses, heart attacks, peripheral arterial diseases and strokes) is still the most frequent cause of death in the western world. Well over half of all the financial resources available for medical care are estimated to be spent for the consequences of arteriosclerosis. To clarify the causes of arteriosclerosis, various theories have been developed, of which the lipid theory is the most highly regarded.

In general, it can be stated that the higher the LDL cholesterol level or level of oxidized LDL cholesterol in the blood, the high the risk of vascular hardening, for example with the consequence of a heart attack. Overweight and hypercholesterolemia are the most important risk factors for the development of arteriosclerosis.

DEFINITIONS AND TERMS

Fats such as cholesterol are soluble neither in water nor blood plasma. To allow them nevertheless to be transported to individual body regions, the fats are bound to particular albuminous substances (proteins) as soon as they occur in the blood. These compounds, comprising lipids (fats) and proteins, are termed lipoproteins.

The "lipoproteins" of the plasma are high-molecular weight water-soluble complex comprising lipids (cholesterol, triglycerides and phospholipids) and apolipoproteins. The cholesterol-containing lipoprotein LDL cholesterol causes arteriosclerosis and is also known as "bad" cholesterol, with the oxidized form of cholesterol being even more dangerous for the body.

"Cholesterol" is synthesized ubiquitously in the body and is an essential component of cell membranes and lipoproteins. In contrast to the triglycerides and phospholipids, which are also synthesized endogenously, the sterol ring of the cholesterol molecule can not be broken down again; cholesterol is transformed into bile acid in the liver or excreted unchanged with the bile into the gut.

In plasma, cholesterol is present as 25 to 40% free (non-esterified) cholesterol and 60 to 75% esterified with unsaturated fatty acids. Both forms together are known as the total cholesterol. Because of the low water solubility, cholesterol is transported in plasma as a complex with apolipoproteins. In the blood, about 70 percent of the total cholesterol is transported via low-density lipoproteins (LDL).

"Triglycerides" are esters of glycerine with three fatty acid residues. In the same way as cholesterol, the triglycerides are also transported in plasma bound to apolipoproteins because of their poor solubility "Lipoproteins" are synthesized in the liver or gut and transport liposoluble substances such as cholesterol in the blood.

Lipoproteins are classified according to their density into five density classes: chylomicrons, very low density lipoproteins (VDL), low density lipoproteins (LDL) and high density lipoproteins (HDL). Chylomicrons, whose physiological concentration in fasting serum, unlike that of other lipoproteins, is very low, are vehicles for transporting exogenous glycerides. The physiological distribution of the other lipoproteins is as follows: VLDL 10%, LDL 70% and HDL 20%. VLDL are the precursors of LDL and vehicles for the transport of endogenous glycerides. LDL are produced by hydrolysis of VLDL. LDL and HDL are both regulators of cellular cholesterol homeostasis, with HDL also regulating lipolysis (splitting of triglycerides into glycerol and free fatty acids). LDL have a diameter of about 20 nm. HDL are the smallest (7-10 nm) and the most protein-rich lipoproteins. Besides native LDL (LDL), oxidized LDL (oxLDL) is also detectable in the blood serum. oxLDL interacts with endogenous plasma proteins, particularly glycoproteins via specific ligands and forms oxLDL glycoprotein complexes.

"Apolipoproteins" are a component of lipoproteins and, together with polar lipids, as a kind of outer shell, surround the lipoprotein core, which is made up of hydrophobic lipids. With the exception of LDL, which only contains apoprotein B, the individual lipoprotein classes have a plurality of apolipoprotein classes with different structures.

Lipoprotein Transport

Cholesterol is principally transported via the two lipoprotein classes LDL and HDL. LDL are primarily responsible for cholesterol transport to peripheral cells that possess specific receptors for LDL. HDL permit and accelerate the removal of cholesterol from the extra-hepatic cells and vessel walls and transfer it to the livers.

Pathology

As regards the pathology of lipid metabolism disorders, it can be said in general that elevations in LDL cholesterol in conjunction with reductions in HDL cholesterol pose the most prominent increased risk of arteriosclerosis. In the pathogeny, LDL, whose particles make a substantial contribution to the formation of atherosclerotic plaques, and HDL therefore play contradictory roles. The quotients of total cholesterol/HDL cholesterol and, in particular, LDL cholesterol/HDL cholesterol are the deciding factors for assessing the risk of heart attack. (Epidemiological studies (Framingham study) also refer to the protective effect of HDL cholesterol.) The secondary diseases of arteriorsclerosis, besides coronary heart disease and peripheral arterial diseases, also include heart and brain infarcts (strokes).

oxLDL, just like LDL, probably causes arteriosclerotic plaques, with oxLDL posing the biggest danger for the body.

But oxLDL also appears to play an important role in other diseases. In patients with chronic kidney failure and diabetes, the concentration of oxLDL glycoprotein complexes is higher than in healthy patients.

LDL is also removed from the blood circulation by the liver and by macrophages. Macrophages are cells of the immune system, which are capable of phagocytosis of larger particles.

The "scavenger pathway" is a known model for explaining how cells engulf particles (phagocytosis). The incorporation of solid particles (debris, foreign bodies, bacteria or LDL plaques) into the cell interior of phagocytes, with subsequent intracellular breakdown, is carried out by phagocytosis. The phagocytic cells are known as phagocytes and consist predominantly of tissue macrophages and mobile blood monocytes.

In phagocytosis, after the particles become attached to the cell membranes of the phagocytes by binding to Fc and complement receptors on the membrane, contractile structures are activated within the cytoplasma. Local inversions of the cell membranes then cause inclusion of the particles in the cytoplasmic vacuoles.

So-called scavenger phagocytes are found in lymph nodes in and along the fibre strands that comprise the medulla.

Whereas the lymph passage from the afferent to the efferent end of the lymph node, particular antigens are removed by the phagocytic cells.

It is further known that the adherence to phagocytic cells, such as polymorphonuclear leucocytes and macrophages, is increased by the attachment of immunoglobulins (Ig) to the surface of bacteria (and other antigens). It is supposed that the increased adherence is effected by attachment of the Fc component of the immunoglobulin to the Fc receptors of the phagocytes. After the antigens have been made "appetizing" by the attachment of (or binding of) antibodies, the complex of antigen and antibodies is taken up and ingested faster by the phagocytic cells. The coating of the antibody surface with immunoglobulins is also known as opsonin-mediated (Fc) adherence, and plays an important role in the immune response.

The antibodies binding to the surface of bacterial cells are capable of fixing particular components of the extracellular liquids. In generic terms, these components are termed the "complement." Animal tests have show that the phagocytosis of cells coated with antibodies is delayed in animals lacking complement. It is thus obvious that opsonization involves a synergy between antibodies and complement.

DESCRIPTION OF THE INVENTION

Drugs of the prior art for reducing LDL cholesterol act by inhibiting the key enzyme for cholesterol synthesis (CSE). For example, one cholesterol synthesis inhibitor is a substance that has become known under the trade name Lipobay. The side effects of CSE inhibitors are generally considerable, including, inter alia, gastrointestinal diseases, sleep disturbances, dizziness, visual disturbances, allergic reactions and hair loss. An approach that is only in the test stage, specifically only in the case of severe familial hypercholesterolemia, is somatic gene therapy, which consists of transferring the gene for the LDL receptor to autogenic liver cells.

So far, no substance that acts as a fat reducer and is largely free of side effects has been available on the market. In particular, no antibodies that induce a severe intracellular accumulation of lipoproteins are so far known. Although the harmful role of lipoproteins in renal diseases (lipid-induced damage of cells of the glomerulus filtration system of the kidney) is known, there is so far no antibody-based therapy of renal diseases, in particular glomerulonecrosis.

The object of the invention consists in the generation of a new substance or of a new substance class for the preparation of a drug for reducing the LDL cholesterol or of the oxLDL cholesterol in humans and animals with the advantageous goal of reducing the risk of infarct.

To achieve this object, a polypeptide is proposed, the amino acid sequence of which is essentially identical to the amino add sequence of SEQ ID NO:1 and/or SEQ ID NO:3, and
  binds the low density lipoproteins (LDL) and/or oxidized LDL (oxLDL), in particular LDL cholesterol and/or oxidized LDL cholesterol (oxLDL cholesterol), The gist of the invention consists in the surprising observation that a purified polypeptide whose sequence corresponds entirely or partly to the light ($V_L$) or heavy chain ($V_H$) of a human monoclonal antibody (SAM 6.10), effects reduction of the low density lipoprotein (LDL) and/or oxLDL. The discovery of this property, which suggests the use of the polypeptide as a fat reducer in a corresponding pharmaceutical formulation, was made in the course of biochemical characterization of the polypeptide. Advantageously, the binding of the polypeptide according to the invention or of the fragments of the polypeptide to LDL and/or oxLDL and to VLDL, the precursors of LDL, is stronger than the binding to HDL. As a result of this property, the polypeptide according to the invention leads to a low value for the respective quotient of LDL/HDL and/or oxLDL/HDL, and thus minimizes the risk of infarct.

The specific binding of the polypeptide to low density lipoproteins (LDL and/or oxLDL), or LDL cholesterol-and/ or oxLDL cholesterol has been proven experimentally by the ELISA method. In the same experiment, it was also possible to prove that the binding of the substance according to the invention to high density lipoproteins (HDL) is weak.

The antibody according to the invention comprises the groups termed $V_L$, $V_H$, Fv, Fc, Fab, Fab', F(ab')$_2$ according to the conventional nomenclature for describing antibodies. The aforementioned groups are also known as fragments. It is entirely possible that an individual fragment is the cause of the fat-reducing effect of the polypeptide according to the invention. In a further development of the substance according to the invention, the substance is a human monoclonal antibody.

The term "functional fragment" in the sense of the invention describes a polypeptide that has at least one of the biological activities that is also shown by the entire polypeptide. In the case of antibodies, it is known, for example, that not all CDR regions are necessary for the specific binding. That is to say that the specific binding of the antibody can be effected by only one CD region, although a total of 3 CD regions are present. The specific binding of the antibody to an antigen can lead, for example, to the induction of apoptosis or to the inhibition of cell proliferation. The biological activity of a functional fragment can be measured by various methods known to the person skilled in the art. A method for measuring the interaction between antibodies and LDL, in particular LDL cholesterol, is the ELISA method.

The complementarity-determining regions (CDRs) of the polypeptide sequence includes the amino acid sequence that is essentially identical to the amino acid sequence Ser-Gly-Asp-Lys-Leu-Gly-Asp-Lys-Tyr-Ala-Cys (CDR1), amino acids 23-33 of SEQ ID NO:1, Gln-Asp-Ser-Lys-Arg-Pro-Ser (CDR2), amino acids 49-55 of SEQ ID NO:1, and Gln-Ala-Trp-Asp-Ser-Ser-Ile-Val-Val (CDR3), amino acids 88-96of SEQ ID NO:1 of the variable region of the light chain (VL); see also Page 2 of the Listing.

The complementarity-determining regions (CDRs) of the peptide sequence include amino acid sequences that are essentially identical to Ser-Tyr-Ala-Met-His (CDR1), Val-Ile-Ser-Tyr-Asp-Gly-Ser-Asn-Lys-Tyr-Tyr-Ala-Asp-Ser-Val-Lys-Gly (CDR2) and Asp-Arg-Leu-Ala-Val-Ala-Gly-Arg-Pro-Phe-Asp-Tyr (CDR3) of SEQ ID No 3 of the variable region of the heavy chain ($V_H$); see also Page 4 of the Listing.

A polypeptide or a nucleic acid sequence is termed "essentially identical" if it has at least 75%, 80%, 85% or 90% [identity] with the amino acid sequence (SEQ ID NO: 1 and 3) quoted as reference or with the nucleic acid sequence (SEQ ID NO: 2 and 4). In a further development of the polypeptide or of the nucleic acid sequence, at least 95%, 98%, 99% or 100% identity in comparison to the quoted references can be demonstrated. For polypeptides, the length of the comparison section will in general have at least 5, 10,15 or desirably at least 20 or 25 sequential amino acids.

The polypeptide according to the invention can be generated by a method known by the name hybridoma technology (Köhler, Millstein, Nature, 1975, Vol. 256 495) and permits the isolation of monoclonal antibodies. It is based on the in-vitro isolation of cellular hybrids that are obtained by the cell fusion of normal lymphocytes with myeloma cells (e.g. HAB-1) of unlimited viability and reproducibility. The hybridoma cells produced in this way have the properties of both parent cells. Correspondingly they have the capability of lymphocytes to produce antibodies (e.g. SAM 6.10) and the capability of myeloma cells for unlimited division and thereby to produce antibodies in large amounts. Each hybrid cell resulting from the fusion produces monoclonal antibodies whose specificity is determined by the original lymphocyte cell. The hybridoma cells are reproduced and then those selected that produce antibodies of the desired specificity. The cultivation of this selection and their isolation leads to antibodies with highly specific reactivity, which only react with particular antigenic determinants.

The evidence of the substantial reduction of the low density lipoprotein (LDL) level (or of the LDL cholesterol level) or of the respective oxidized form in the blood plasma has been confirmed in an animal experiment without the HDL level in the detectable range falling. An essential feature of these is that the vital functions of the animals are not affected during administration of the antibody, so that the substance according to the invention can so far be described as free of side effects. (The mechanism of the antibody according to the invention could be explained by analogy with the mechanism of the known scavenger pathway.)

Another indication for the use of the medicament according to the invention is the treatment of renal diseases, in particular glomerulonecrosis (glomerulosclerosis).

It lies within the scope of the invention that the polypeptide according to the invention is preferably used in purified form for the preparation of the drug, all methods known to a person skilled in the art (e.g. affinity chromatography, gel filtration) coming into consideration for purification. As indication of the substance according to the invention, the fat-reducing effect is foremost, with emphasis on the selective reduction of LDL or LDL-cholesterol. As a result of the property of binding LDL and/or oxLDL more strongly than HDL, the polypeptide according to the invention leads to a low value for the quotients of LDL/HDL and/or oxLDL/HDL, and thus minimizes the infarct risk.

The adjuvants and carrier substances for preparing a drug are known to a person skilled in the art and can be produced by conventional means (see Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Material and Methods

Immortalization of Lymphocytes and Primary Testing of the Antibodies

The lymphocytes are immortalized by fusing with the heteromyeloma HAB-1 (Faller et. al, 1990) according to the standard protocol and incubating. In summary, lymphocytes are fused with HAB-1 cells by means of PEG. The triomes are seeded on four 24-well plates. The average growth frequency is 80-90%; 50% of the growing clones secrete immunoglobulins. The first testing of the secreted human monoclonal antibodies was carried out by ELISA to determine the isotype. The human monoclonal antibodies can subsequently by analyzed by immunohistochemical, genetic, biochemical and molecular biological techniques.

Required Materials:
RPMI 1640 (PAA company) without supplements RPMI 1640 with HAT supplement (HAT-Supplement, PAA company) and 10% FCS, 1% glutamine and 1% penicillin/streptomycin Wash HAB-1 (fusion partner) twice with RPMI without supplements Centrifuge for 5 min. at 1,500 rpm thaw out frozen lymphocytes (from spleen, lymph nodes or blood) and wash twice with RPMI without supplements; also centrifuge.

Suspend the two pellets in 10 ml RPMI without supplement each, and count in the Neubauer counting chamber Fuse Hab-1 to lymphocytes in a ratio of 1:2-1:3

Bring the cell pellets together after the second washing, mix and centrifuge for 8 min. at 1,500 rpm Carefully drip the PEG (Polyethylene Glycol 1500, from Roche), which was previously heated to 37° C., onto the pellet with gentle rotary movement of the 50 ml test tube Resuspend slightly and then allow to rotate for exactly 90 s in the water bath at 37° C.

Then wash out the PEG with RPMI without supplements (two full 10 ml pipettes)

Centrifuge for 5 min. at 1,500 rpm

Plate-out the 24-well plates with 1 ml per well of RPMI with HAT supplement (HAT=hypoxanthine, aminopterine, thymidine)

Dissolve the pellet in RPMI with HAT supplement

Pipette one half-ml of the cells in each case into a 24-well plate

Place the fusion plates in the incubator

Exchange the medium with RPMI with HAT supplement once per week

Purification of the SAM 6.10 Antibody

Purification of the culture supernatant by cation-exchange chromatography via FPLC For this purpose, the hybridoma cells producing the SAM-6.10 lgM antibodies (DSM ACC2903, deposited Apr. 3, 2008, DSMZ, Inhoffenstr. 7B D-38124 Braunschweig) were cultured in a special serum-free cell culture medium (AIMV medium, Gibco) and the lgM content in the culture supernatant was determined by nephelometry. For purification, the culture supernatant was adjusted to a pH of 5.9 and the solution filtered. For binding, a special cationic column (Hi-Trap™ SP FF column, 5 ml, Amersham Bioscience) was used. The column was equilibrated with filtered buffer A (20 mM phosphate buffer, pH 5.9) at the beginning of purification. Then the culture supernatant cooled on ice was applied to the column at a flow rate of 1 ml/min. After application of the supernatant, the column was washed with buffer A for 20 min at a flow rate of 2 ml/min, until a constant base line so that not all bound proteins are removed. Subsequently the antibodies bound to the column were eluted by admixing buffer B (20 mM phosphate buffer, 1 M NaCl, pH 8.0) and collected in fractions. The SAM-6.10 antibody (lgM) content in the individual fractions was subsequently determined by nephelometry and the purity and intactness of the purified antibody was tested by SDS-PAGE and western blot analysis.

Measurement of oxLDL

Measurement is carried out by means of the Oxidized LDL ELISA test kit from Mercodia, Uppsala, Sweden. Test principle: Oxidized LDL ELISA is a solid phase two-site enzyme immunoassay. It is based on the direct sandwich technique in which two monoclonal antibodies are directed against a specific antigen on oxidized LDL apolipoprotein B. During incubation, oxidized LDL in the sample reacts with anti-oxidized LDL antibodies bound to wells in the microtitre plate. After washing, in which the non-reactive components of the sample are removed, a peroxidase-conjugated anti-human apolipoprotein B antibody detects the oxidized LDL that is bound to the solid phase. After a second incubation and washing, which removes the antibodies marked with the unbound enzyme, the conjugate is detected by reaction with 3, 3', 5,5' tetramethylbenzidine (TMB). The reaction is stopped by the addition of acid to define a calorimetric end point, which is read spectrophotometrically at 450 nm.

Measurement of the Binding of SAM-6 to oxLDL

An ELISA plate (Becton Dickinson Labare Europ, France) was incubated overnight at 4° C. with the LDL fractions oxidized to different extents. The non-specific binding sites were blocked with RPMI 1640 medium containing 10% FCS for 1 h. Then the plate was incubated with 60 µg/ml SAM-6 antibody for one hour at 37° C. After washing three times with PBS, the ELISA plate was incubated for 1 h with HRP-coupled secondary antibody (rabbit anti human lgM, Dako Hamburg, Germany, 1:1000 in PBS). Then the plate was washed again with PBS and citrate buffer, OPD (DakoCytomation, Glostrup, Denmark) added and the colour change at 490 nm was measured with an ELISA reader.

Flow Cytometry (FACS Analysis)

The adherent cells used were detached from the base of the culture bottles by treatment with trypsin/EDTA) The reaction was stopped with 10 ml RPMI 1640 medium (+supplements) and the cells were pelleted at 1000×g for 5 min. The cells were washed twice with PBS, suspended in FACS buffer (PBS, 0.01% Na azide) and put on ice for 30 min to reconstitute the cell membranes. Then the cells were adjusted to a density of $1\times10^6$ cells/ml and 200 µl of the cell suspensions were transferred to the FACS reaction vessels so that there was a cell count of $2\times10^5$ cells per test tube. The cells were pelleted for 5 min. at 4° C. and 1,400 rpm, the pellets resuspended and incubated with the primary antibodies for 15 min. on ice. As primary antibodies, 100 µg/ml SAM-6 antibodies in FACS buffer (total volume 200 µl) or 100 mg/ml LDL were used. 100 µg/ml Chrompure human lgM acted as isotype control. Alternatively, the cells were preincubated with LDL for 30 min. and then 100 µg/ml SAM-6 antibodies added for 15 min.

After incubation, the cells were centrifuged off; the supernatant was discarded and the pellets were washed with 500 µl cold FACS buffer. This was followed by a 15-minute light-protected incubation with the FITC-coupled secondary antibody (rabbit anti human lgM, FITC-coupled, 1:50 in FACS buffer for SAM-6 or Chrompure human lgM). After washing again, the cells were suspended in 200 µl cold FACS buffer and stored, light-protected, on ice until measurement. Measurement was carried out by means of a flow cytometer (FACScan; Becton Dickinson, USA).

Animal Experiments for Demonstrating the in vivo Effect of the SAM 6.10 Antibody Experiment 1: 500 µg purified SAM 6.10 antibodies was injected intraperitoneally. The LDL concentration in the blood serum was measured after 2 days (see below for method).

Experiment 2: as above

Experiment 3: 1 mg purified SAM 6.10 antibodies was injected intraperitoneally. The LDL concentration in the blood serum was measured after 14 days.

Control A: Normal values control mouse
Control B: Normal values control mouse

The serum concentration of LDL is significantly reduced in the mice treated with SAM 6.10 (see FIGS. 10 and 11).

Toxicity

500 µg and 1 mg respectively of purified SAM 6.10 antibodies was injected intraperitoneally into mice.

no acute toxicity no latent toxicity (period 3 months).

The organs of the dead mice from experiments 1, 2 and 3 (see above) were removed and investigated: The liver, lung, heart, spleen, small intestine, large intestine, kidneys, stomach and brain did not show any morphological changes. The organs were furthermore investigated immunohistochemically for any lipid deposits. Staining with Sudan III did not show lipid deposits in any organ.

The organs of the sacrificed mice were fixed in formalin and embedded in paraffin. Staining was carried out with Sudan III dye according to the following protocol:

Sudan III Staining on Paraffin Sections/for Macrophages
Deparaffining:
Xylene 1 5 min.
Xylene 2 5 min.
100% Ethanol 1 5 min
100% Ethanol 2 5 min
Methanol 70 ml +$H_2O_2$ 500 µl 5 min
90% Ethanol 1 3 min
90% Ethanol 2 3 min
80% Ethanol 1 3 min
80% Ethanol 2 3 min
70% Ethanol 1 3 min
70% Ethanol 2 3 min
Place sections in PBS
Incubate sections for 15 min with Sudan III
Wash with aqua dest.
Immerse 1× in 60% isopropanol
Wash with aqua dest.
Counter stain with haemalaun for 6 min.
Soak sections for 10 min, wash with aqua dest and mount in glycerine gelatine For Sudan III staining of macrophages, the adherent macrophages are grown on object slides and then treated with the corresponding reagents. Staining is carried out as follows:

Fix the cells in 60% isopropanol (6 min)
Incubate for 20 min with Sudan III
Wash with aqua dest.
Counterstain with haemalaun for 6 min
Soak sections for 10 min, wash with aqua dest and mount in glycerine gelatine Determination of Lipids in Blood Samples Measurement of the various lipids in blood serum was carried out automatically with the MODULAR D P800 instrument (Roche). Determination of the LDL cholesterol value was carried out by enzymatic colorimetry (CHOD/PAP) without sample pre-treatment.

Test Principle for Determining the Lipid Concentration in Serum:

HDL, VLDL and chylomicrons are selectively hydrolysed by a detergent 1. The cholesterol liberated in these lipoproteins reacts immediately as a result of the enzymatic action of the cholesterolesterase (CE) and cholesteroloxidase (CHOD), and hydrogen peroxide is produced. The latter forms a colourless product with 4-aminoantipyridine in the presence of a peroxidase (POD). During this step, the LDL particles remain intact. The reaction of LDL cholesterol is initiated by the addition of detergent 2 and the coupling substance N,N-bis(4-sulphobutyl)-m-toluidine (DSBmT). The second detergent liberates cholesterol in the LDL particles. in the enzymatic reaction, a dye is formed in the presence of the coupling substance. The intensity of the red quinine imine dye formed is directly proportional to the LDL cholesterol concentration. It is determined by measuring the increase of extinction at 552 nm.

ELISA (LDL/HDL)

Precoat the ELISA plate with LDL (Lipoprotein low density from Human Plasma, Sigma, 10 µg/ml in PBS) or HDL (human HDL, Chemicon, 10 µg/ml in PBS)→50 µl per well Cover plate and store overnight at 4° C.

Next day, wash plate 2× with PBS

Pipette 100 nl of RPMI into each well and incubate for 1 h at room temperature

Then wash 2× with PBS

Pipette 50 µl in each case of the respective positive controls into 2 wells (double determination) Positive control: Mab to human LDL mouse IgG2a 1:1000 in PBS Alongside, 50 µl RPMI as negative control (double determination)

Pipette 50 µl of the samples (supernatant SAM6.10) (double determination) side by side Incubate for 1 h in the incubator Wash 2× with PBS Wash 2× with PBS/0.05% Tween Wash 2× with PBS Pipette 50 µl of the respective second AK (peroxidase conjugated): Rabbit anti human IgM 1:1000 in PBS/ 0.05% Tween (for SAM 6.10) Rabbit anti mouse IgGs 1:1000 with PBS Tween (for positive control LDL)

Incubate for 1 h in the incubator

Wash 2× with PBS

Wash 1× with PBS/0.05% Tween

Wash 2× with PBS

Wash 2× with citrate buffer

For evaluation: Dissolve OPD tablet (Dako, Hamburg) in citrate buffer+$H_2O_2$ (3 ml citrate buffer+one tablet+5 µl $H_2O_2$)

Pipette 50 µl dye into each well

When there is a positive reaction yellow coloration), stop with 10 µl 3 M $H_2SO_4$ Sequence listing Page 1 of the Listing shows the amino acid sequences (SEQ ID NO:1) of the variable region of the light chain ($V_L$).

Page 2 of the Listing shows the nucleotide acid sequences (SEQ ID NO:2) of the variable region of the light chain ($V_L$). The complementarity-determining regions (CDRs) are indicated by horizontal lines and are substantially identical to nucleotides 67-99 (CDR1), 145-165 (CDR2) and 262-288 (CDR3) of SEQ ID NO:2.

Page 3 of the Listing shows the amino acid sequences (SEQ ID NO:3) of the variable region of the heavy chain ($V_H$).

Page 4 of the Listing shows the nucleotide acid sequence (SEQ ID NO:4) of the variable region of the heavy chain ($V_H$). The complementarity-determining regions (CDRs) are indicated by horizontal lines and are substantially identical to nucleotides 91-105 (CDR1), 148-198 (CDR2) and 295-330 (CDR3) of SEQ ID NO:4.

Cell-biological experiments

DESCRIPTION OF FIGURES

The figures explained below are not intended to restrict the invention, but only to explain it and prove its feasibility with reference to examples.

Figure 3A shows the binding of LDL to macrophages. Figure 3B proves that the human monoclonal antibody SAM-6, too, binds to macrophages. The proof of binding of a control IgM to macrophages in Figure 3C demonstrates that the macrophages possess µ receptors. The rightward shift of the signal in Figure 3D demonstrates that simultaneous incubation of LDL and SAM-6 effect a multiple binding of SAM-6 to the cells.

FIG. 4 shows cells that were incubated for 48 h with either SAM-6 or an IgM control antibody and subsequently subjected to Sudan III staining. The cells incubated with the antibody SAM-6 show, by their red coloration, distinct deposition of neutral fats. The cells incubated with the control antibody by contrast show no changes.

Figure 1:
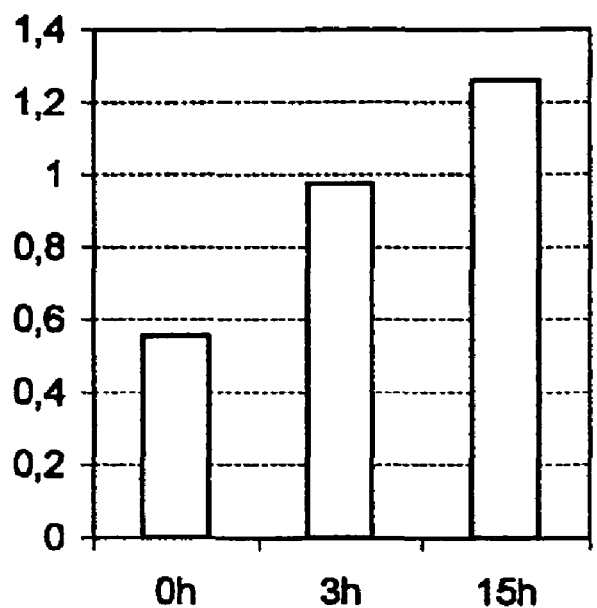
FIG. 1 shows the measurement of oxLDL in dependence on the incubation time with a copper sulphate solution. In the experiment, LDL (Sigma, Taufkirchen, Germany) was oxidized for 3 and 15 h respectively by incubation with 20 µM $CuSO_4$. The amount of oxidized LDL was determined with the Mercodia Oxidized LDL ELISA, according to the instructions for use. It can be clearly seen that the amount of oxidized LDL increases with increasing incubation time, with each LDL fraction that was not treated with copper ions being already partly present in oxidized form. After 15 hours' incubation, the proportion of oxidized LDL has approximately doubled.
Figure 2:
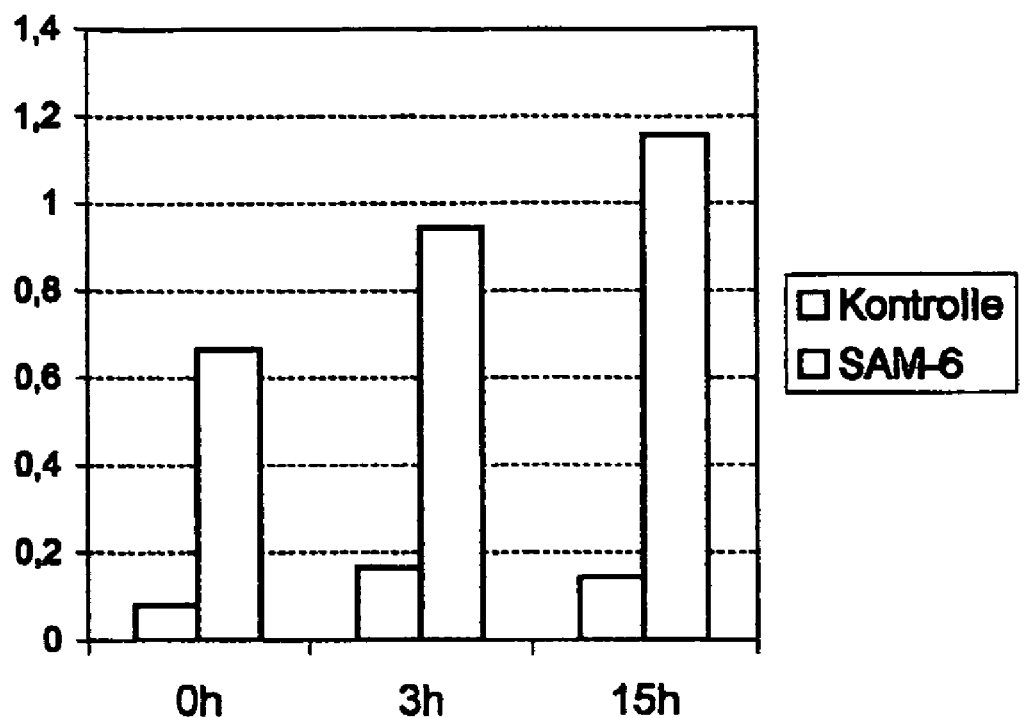
FIG. 2 shows the proof of binding of SAM-6 to oxLDL. To prove binding of SAM-6 to oxLDL by means of the ELISA binding assay, the ELISA plate was precoated with LDL fractions oxidized to different degrees before the primary antibody SAM-6 and the secondary antibody anti-human IgM, required for detection purposes, were added. The result shows that the more LDL that is present in its oxidized form, the more strongly the antibody SAM-6 according to the invention binds.
Figure 3:
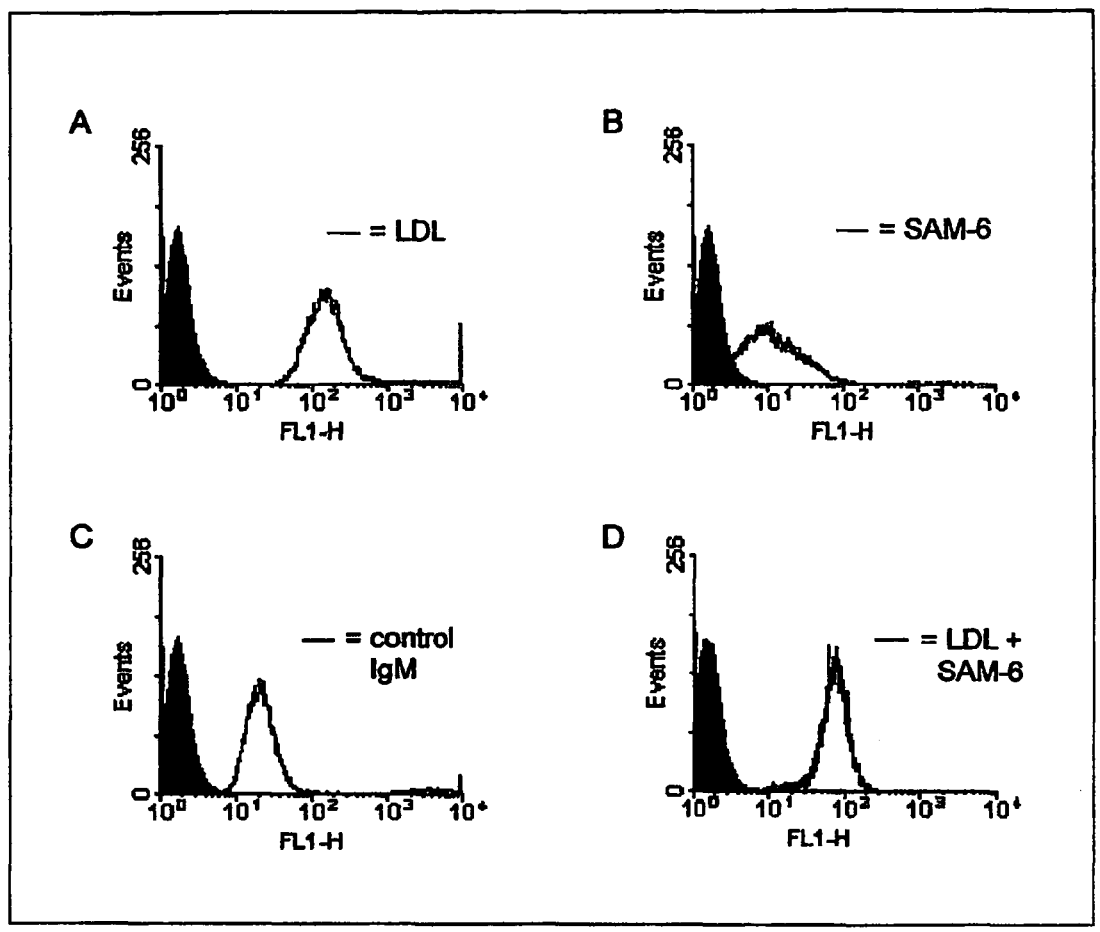
FIG. 3 shows the result of an FACS analysis. The cells used for this purpose are of the mouse macrophage cell line P388D1(IL-1) (DSMZ Accession No. ACC 288).
Figure 4:
FIGS. 4 and 5 show the result of the Sudan III staining, for which the cells of the mouse macrophage cell line P388D1 (IL-1) were used. Figure g
Figure 5:
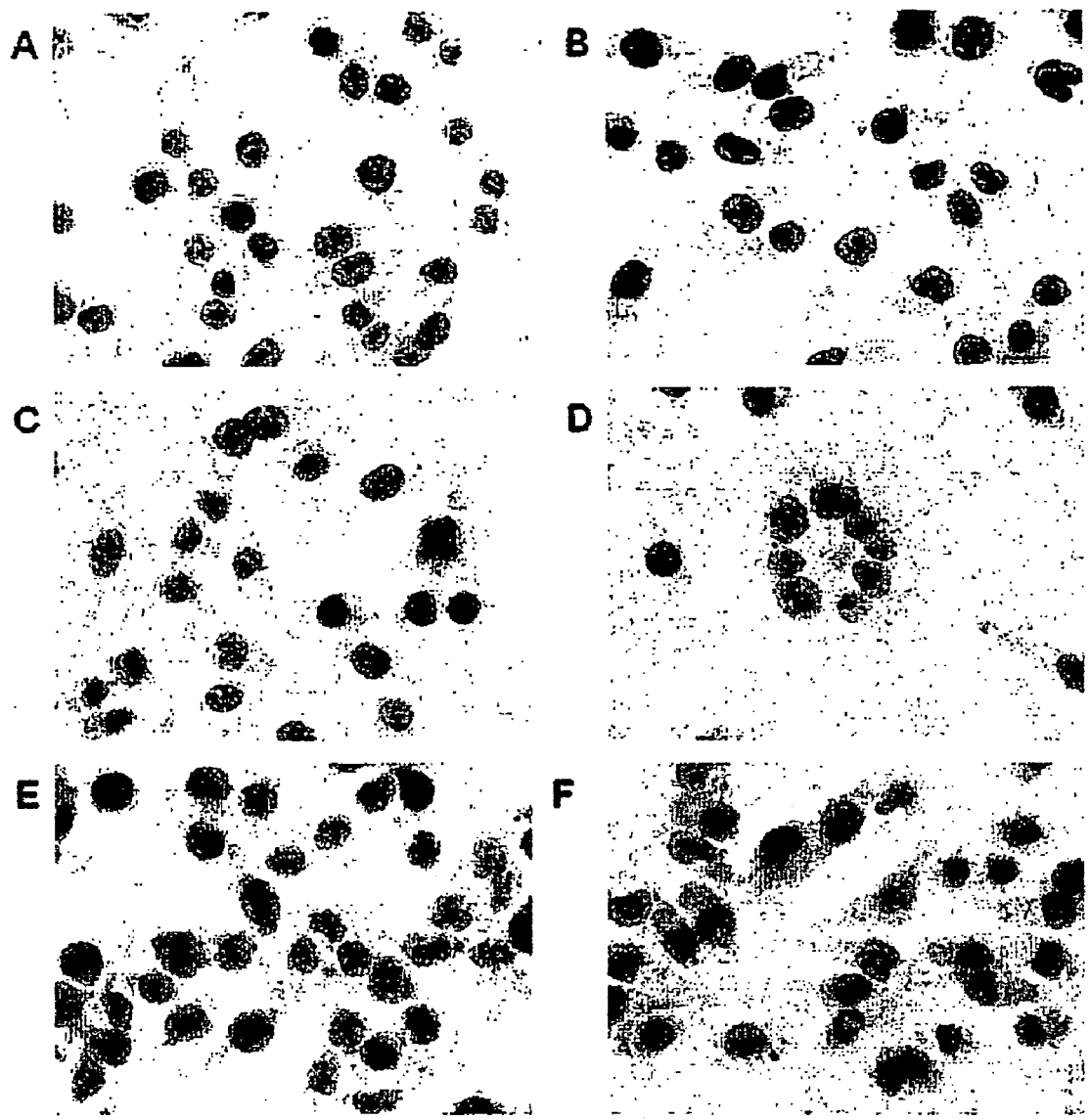

For the stains shown in FIG. 5, the macrophages were cultivated for 24 h both with and without FCS supplement. Then, for a further 24 h, either only LDL, or only SAM-6, or LDL and SAM-6 together were respectively added. Subsequently staining with Sudan III was carried out. The left figure column with the FIGS. 5A, 5C and 5E show cells that were cultivated without supplementation of FCS. The right image column with the FIGS. 5B, 5D and 5F show cells that were cultivated with supplementation of FCS.

FIGS. 5A and 5B demonstrate that both macrophages that were cultivated without FCS and macrophages that have grown in the presence of FCS show basal deposition of neutral fats. Figure 5C demonstrates that when SAM-6 is supplemented to macrophages that were cultivated without FCS, no fat deposition is evident. As shown in Figure 5D, on the other hand, a reinforced lipid accumulation is observed in macrophages that were cultivated with FCS and subsequently had SAM-6 added to them.

FIGS. 5E and 5F demonstrate that, with a co-incubation of SAM-6 and LDL, the intracellular lipid accumulation increases substantially both in macrophages that were cultivated with FCS and in those that have grown without the addition of FCS.

Figure 6:
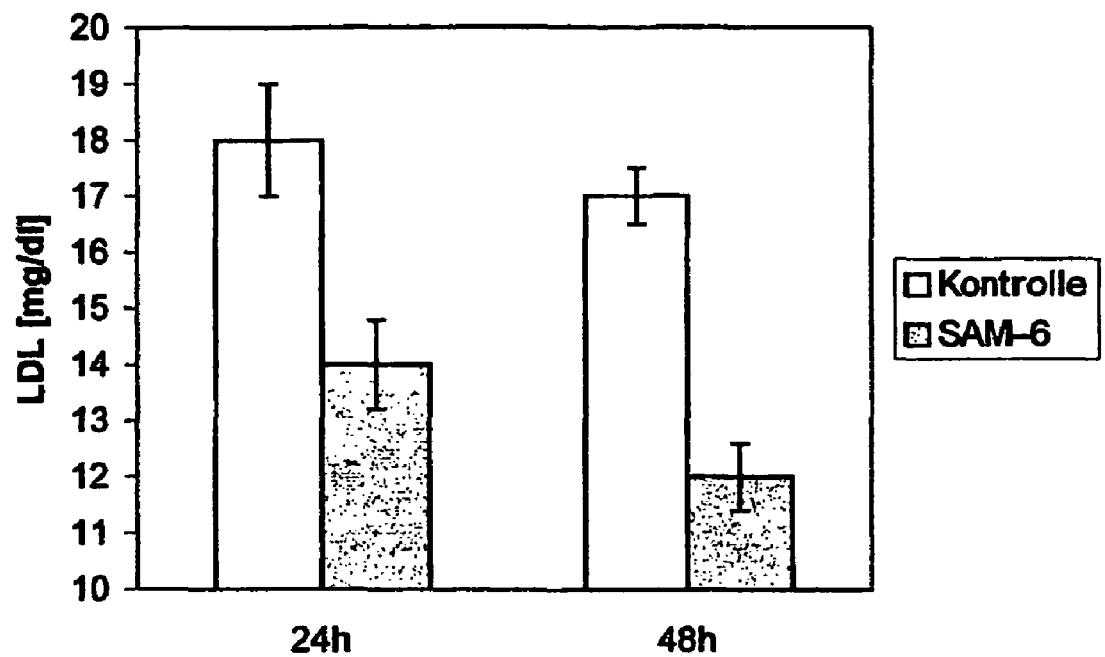

FIG. 6 shows the effect of the antibody SAM-6 on LDL values in vivo. In the experiment, 1 mg of purified SAM-6 antibodies and, in the control experiment, 1 mg of human Chrompure IgM (isotype control) were injected into the mice intraperitoneally. The LDL concentration in the blood was measured after 24 and 48 h. After 24 and 48 hours, a clear reduction of serum LDL can be observed in the mice treated with SAM-6.

The measurement of LDL in the blood serum was carried out automatically with the MODULAR D P800 instrument (Roche), the plotted values being obtained as a result of the "LDL Cholesterol Direct" diagnostic kit (Roche Diagnostics).

Figure 7:
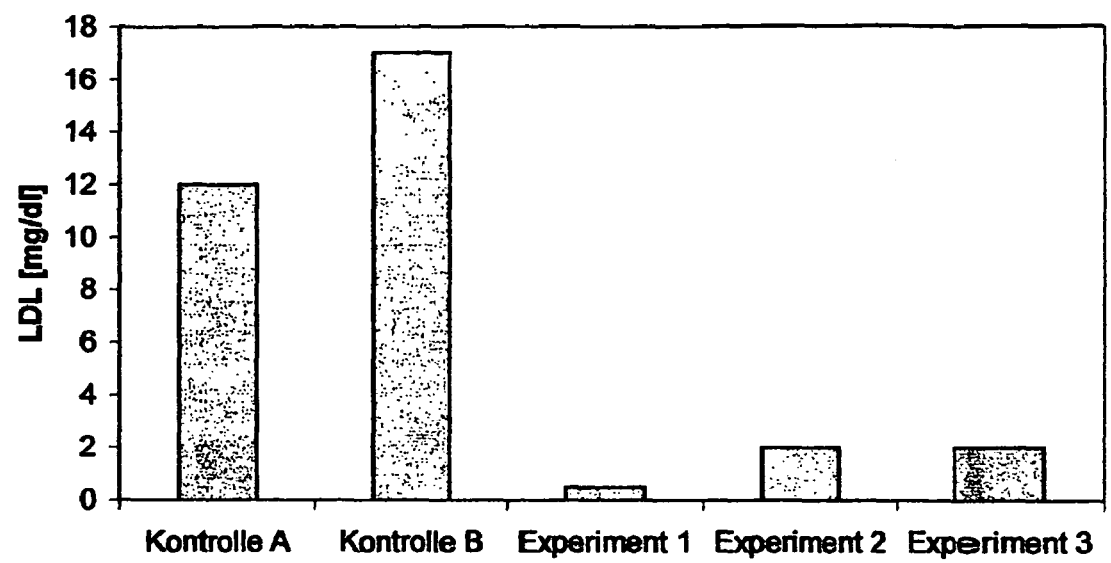

FIG. 7 also demonstrates the in vivo effect of SAM-6.10, an indirect method according to the Friedewald formula being used to calculate the values. Here, the amount of LDL is calculated from the difference between total cholesterol, HDL and triglycerides. According to this manner of evaluating the experiment, the reduction of the concentration of LDL in the serum after SAM 6.10 treatment is even greater. However, this indirect measurement method must be regarded as less accurate in comparison to the method used in FIG. 6.

The invention claimed is:

1. A purified antibody or functional fragment thereof, comprising a light chain ($V_L$) variable region sequence and a heavy chain ($V_H$) variable region sequence:
wherein the heavy chain ($V_H$) variable region sequence comprises an amino acid sequence at least 90% identical to the amino acid sequence of SEQ ID NO.:3, wherein said antibody or functional fragment thereof binds to apolipoprotein B containing low density lipoproteins (LDL) and apolipoprotein B containing oxidized LDL (oxLDL).

2. The purified antibody or functional fragment thereof according to claim 1, wherein said antibody or functional fragment thereof binds to apolipoprotein B containing LDL cholesterol and binds to apolipoprotein B containing oxidized LDL cholesterol (oxLDL cholesterol).

3. The purified antibody or functional fragment thereof according to claim 1, wherein said apolipoprotein B containing low density lipoproteins (LDL) or said apolipoprotein B containing oxidized LDL (oxLDL) occur in humans.

4. The purified antibody or functional fragment thereof according to claim 1, wherein said antibody or functional fragment thereof is a functional fragment of said antibody.

5. The purified antibody or functional fragment thereof according to claim 1, wherein said functional fragment is selected from the group consisting of $F_v$, Fab, Fab' and $F(ab')_2$.

6. The purified antibody or functional fragment thereof according to claim 1, wherein the light chain ($V_L$) variable region sequence is at least 80% identical to SEQ ID NO:1.

7. The purified antibody or functional fragment thereof according to claim 5, wherein said functional fragment contains an amino acid fragment of the light chain ($V_L$) variable region or the heavy chain ($V_H$) variable region amino acid sequence of SEQ ID NO:1 or SEQ ID NO:3.

8. The purified antibody or functional fragment thereof according to claim 1, wherein said light chain ($V_L$) variable region sequence is at least 85% identical to the amino acid sequence of SEQ ID NO:1.

9. The purified antibody or functional fragment thereof according to claim 1, wherein said heavy chain ($V_H$) variable region sequence is at least 95% identical to the amino acid sequence of SEQ ID NO:3.

10. The purified antibody or functional fragment thereof according to claim 1, wherein said light chain ($V_L$) variable region sequence is at least 90% identical to SEQ ID NO:1.

11. The purified antibody or functional fragment thereof according to claim 1, wherein said heavy chain ($V_H$) variable region sequence is at least 98% identical to SEQ ID NO:3.

12. The purified antibody or functional fragment thereof according to claim 1, wherein said antibody or functional fragment thereof is a monoclonal antibody.

13. The purified antibody or functional fragment thereof according to claim 1, wherein said antibody or functional fragment thereof is produced by a hybridoma.

14. The purified antibody or functional fragment thereof according to claim 1, wherein said light chain ($V_L$) variable region sequence of the antibody or functional fragment contains a sequence at least 95% identical to SEQ ID NO:1.

15. The purified antibody or functional fragment thereof according to claim 1, wherein said light chain ($V_L$) variable region sequence of the antibody or functional fragment contains a sequence at least 98% identical to SEQ ID NO:1.

16. The purified antibody or functional fragment thereof according to claim 1, wherein said heavy chain ($V_H$) variable region sequence of the antibody or functional fragment contains a sequence at least 99% identical to SEQ ID NO:3.

17. A purified antibody or functional fragment thereof comprising a light chain ($V_L$) variable region sequence and a heavy chain ($V_H$) variable region sequence, wherein the light chain ($V_L$) and heavy chain variable region sequences comprise SEQ ID NO:1 or SEQ ID NO:3, respectively, and wherein said antibody or functional fragment thereof binds to apolipoprotein B containing low density lipoproteins (LDL) and apolipoprotein B containing oxidized LDL (oxLDL).

18. A purified antibody or functional fragment thereof, wherein the heavy chain ($V_H$) variable region sequence comprises a complementary-determining region (CDR) set forth as [Ser-Tyr-Ala-Met-His (CDR1) amino acids 31-35 of SEQ ID NO:3, and Val-Ile-Ser-Tyr-Asp-Gly-Ser-Asn-Lys-Tyr-Tyr-Ala-Asp-Ser-Val-Lys-Gly (CDR2) amino acids 50-66 of SEQ ID NO:3, and Asp-Arg-Leu-Ala-Val-Ala-Gly-Arg-Pro-Phe-Asp-Tyr (CDR3) amino acids 99-110 of SEQ ID NO:3.], and
wherein said antibody or functional fragment thereof binds to apolipoprotein B containing low density lipoproteins (LDL) and apolipoprotein B containing oxidized LDL (oxLDL).

19. The purified antibody or functional fragment thereof according to claim 18, wherein said heavy chain ($V_H$) variable region sequence of the antibody or functional fragment contains a sequence at least 90% identical to SEQ ID NO:3.

20. The purified antibody or functional fragment thereof according to claim 18, wherein the light chain ($V_L$) variable region sequence comprises Ser-Gly-Asp-Lys-Leu-Gly-Asp-Lys-Tyr-Ala-Cys (CDRI), amino acids 23-33 of SEQ ID NO:1, Gln-Asp-Ser-Lys-Arg-Pro-Ser (CDR2), amino acids 49-55 of SEQ ID NO:1, or Gln-Ala-Trp-Asp-Ser-Ser-Ile-Val-Val (CDR3), amino acids 88-96 of SEQ ID NO:1.

21. The purified antibody or functional fragment thereof according to claim 18, wherein the light chain ($V_L$) variable region sequence comprises Ser-Gly-Asp-Lys-Leu-Gly-Asp-Lys-Tyr-Ala-Cys (CDR1), amino acids 23-33 of SEQ ID NO:1, Gln-Asp-Ser-Lys-Arg-Pro-Ser (CDR2), amino acids 49-55 of SEQ ID NO:1, and Gln-Ala-Trp-Asp-Ser-Ser-Ile-Val-Val (CDR3), amino acids 88-96 of SEQ ID NO:1.

22. A purified antibody or functional fragment thereof, wherein the heavy chain ($V_H$) variable region sequence comprises Ser-Tyr-Ala-Met-His (CDR1), amino acids 31-35 of SEQ ID NO:3, Val-Ile-Ser-Tyr-Asp-Gly-Ser-Asn-Lys-Tyr-Tyr-Ala-Asp-Ser-Val-Lys-Gly (CDR2), amino acids 50-66 of SEQ ID NO:3, and Asp-Arg-Leu-Ala-Val-Ala-Gly-Arg-Pro-Phe-Asp-Tyr (CDR3), amino acids 99-110 of SEQ ID NO:3, and wherein said antibody or functional fragment thereof binds to apolipoprotein B containing low density lipoproteins (LDL) and apolipoprotein B containing oxidized LDL (oxLDL).

23. A purified polypeptide, comprising a heavy chain ($V_H$) variable region sequence at least 90% identical to the amino acid sequence of SEQ ID NO.:3, wherein said polypeptide binds to apolipoprotein B containing low density lipoproteins (LDL) and apolipoprotein B containing oxidized LDL (oxLDL).

24. The purified polypeptide of claim 23, wherein the heavy chain ($V_H$) variable region sequence is at least 95% identical to the amino acid sequence of SEQ ID NO.:3, and wherein said polypeptide binds to apolipoprotein B containing low density lipoproteins (LDL) and apolipoprotein B containing oxidized LDL (oxLDL).

25. The purified polypeptide of claim 23, wherein the heavy chain ($V_H$) variable region sequence is at least 98% identical to the amino acid sequence of SEQ ID NO.:3, and wherein said polypeptide binds to apolipoprotein B containing low density lipoproteins (LDL) and apolipoprotein B containing oxidized LDL (oxLDL).

26. The purified polypeptide of claim 23, wherein the heavy chain ($V_H$) variable region sequence is at least 99% identical to the amino acid sequence of SEQ ID NO.:3, and wherein said polypeptide binds to apolipoprotein B containing low density lipoproteins (LDL) and apolipoprotein B containing oxidized LDL (oxLDL).

27. The purified polypeptide of claim 23, wherein the heavy chain ($V_H$) variable region sequence comprises [Ser-Tyr-Ala-Met-His (CDR1) amino acids 31-35 of SEQ ID NO:3, and Val-Ile-Ser-Tyr-Asp-Gly-Ser-Asn-Lys-Tyr-Tyr-Ala-Asp-Ser-Val-Lys-Gly (CDR2) amino acids 50-66 of SEQ ID NO:3, and Asp-Arg-Leu-Ala-Val-Ala-Gly-Arg-Pro-Phe-Asp-Tyr (CDR3) amino acids 99-110 of SEQ ID NO:3.

* * * * *

SEQUENCE LISTING

```
<160> NUMBER OF SEQ ID NOS: 4

<210> SEQ ID NO 1
<211> LENGTH: 96
<212> TYPE: PRT
<213> ORGANISM: Homo sapiens
<220> FEATURE:
<221> NAME/KEY: misc_feature
<223> OTHER INFORMATION: variable region of the light chain (VL) of
      antibody SAM-6

<400> SEQUENCE: 1

Ser Tyr Val Leu Thr Gln Pro Pro Ser Val Ser Val Ser Pro Gly
1               5                   10                  15

Gln Thr Ala Ser Ile Thr Cys Ser Gly Asp Lys Leu Gly Asp Lys
                20                  25                  30

Tyr Ala Cys Trp Tyr Gln Gln Lys Pro Gly Gln Ser Pro Val Leu
                35                  40                  45

Val Ile Tyr Gln Asp Ser Lys Arg Pro Ser Gly Ile Pro Glu Arg
                50                  55                  60

Phe Ser Gly Ser Asn Ser Gly Asn Thr Ala Thr Leu Thr Ile Ser
                65                  70                  75

Gly Thr Gln Ala Met Asp Glu Ala Asp Tyr Tyr Cys Gln Ala Trp
                80                  85                  90

Asp Ser Ser Ile Val Val
                95

<210> SEQ ID NO 2
<211> LENGTH: 288
<212> TYPE: DNA
<213> ORGANISM: Homo sapiens
<220> FEATURE:
<221> NAME/KEY: misc_feature
<223> OTHER INFORMATION: variable region of the light chain (VL) of
      antibody SAM-6

<400> SEQUENCE: 2 tcc tat gtg ctg act cag cca ccc tca gtg tcc gtg tcc cca gga         45
Ser Tyr Val Leu Thr Gln Pro Pro Ser Val Ser Val Ser Pro Gly
1               5                   10                  15 cag aca gcc agc atc acc tgc tct gga gat aaa ttg ggg gat aaa         90
Gln Thr Ala Ser Ile Thr Cys Ser Gly Asp Lys Leu Gly Asp Lys
                20                  25                  30 tat gct tgc tgg tat cag cag aag cca ggc cag tcc cct gtg ctg        135
Tyr Ala Cys Trp Tyr Gln Gln Lys Pro Gly Gln Ser Pro Val Leu
                35                  40                  45 gtc atc tat caa gat agc aag cgg ccc tca ggg atc cct gag cga        180
Val Ile Tyr Gln Asp Ser Lys Arg Pro Ser Gly Ile Pro Glu Arg
                50                  55                  60 ttc tct ggc tcc aac tct ggg aac aca gcc act ctg acc atc agc        225
Phe Ser Gly Ser Asn Ser Gly Asn Thr Ala Thr Leu Thr Ile Ser
                65                  70                  75 ggg acc cag gct atg gat gag gct gac tat tac tgt cag gcg tgg        270
```

-continued

```
Gly Thr Gln Ala Met Asp Glu Ala Asp Tyr Tyr Cys Gln Ala Trp
            80                  85                  90 gac agc agc att gtg gta                                              288
Asp Ser Ser Ile Val Val
                95
```

<210> SEQ ID NO 3
<211> LENGTH: 110
<212> TYPE: PRT
<213> ORGANISM: Homo sapiens
<220> FEATURE:
<221> NAME/KEY: misc_feature
<223> OTHER INFORMATION: variable region of the heavy chain (VH) of
      antibody SAM-6

<400> SEQUENCE: 3

```
Gln Val Gln Leu Val Glu Ser Gly Gly Gly Val Val Gln Pro Gly
1               5                   10                  15

Arg Ser Leu Arg Leu Ser Cys Ala Ala Ser Gly Phe Thr Phe Ser
                20                  25                  30

Ser Tyr Ala Met His Trp Val Arg Gln Ala Pro Gly Lys Gly Leu
                35                  40                  45

Glu Trp Val Ala Val Ile Ser Tyr Asp Gly Ser Asn Lys Tyr Tyr
                50                  55                  60

Ala Asp Ser Val Lys Gly Arg Phe Thr Ile Ser Arg Asp Asn Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Asp Arg Leu Ala Val Ala Gly
                95                  100                 105

Arg Pro Phe Asp Tyr
                110
```

<210> SEQ ID NO 4
<211> LENGTH: 330
<212> TYPE: DNA
<213> ORGANISM: Homo sapiens
<220> FEATURE:
<221> NAME/KEY: misc_feature
<223> OTHER INFORMATION: variable region of the heavy chain (VH) of
      antibody SAM-6

<400> SEQUENCE: 4

```
cag gtg cag ctg gtg gag tct ggg gga ggc gtg gtc cag cct ggg          45
Gln Val Gln Leu Val Glu Ser Gly Gly Gly Val Val Gln Pro Gly
1               5                   10                  15 agg tcc ctg aga ctc tcc tgt gca gcc tct gga ttc acc ttc agt          90
Arg Ser Leu Arg Leu Ser Cys Ala Ala Ser Gly Phe Thr Phe Ser
                20                  25                  30 agc tat gct atg cac tgg gtc cgc cag gct cca ggc aag ggg ctg         135
Ser Tyr Ala Met His Trp Val Arg Gln Ala Pro Gly Lys Gly Leu
                35                  40                  45 gag tgg gtg gca gtt ata tca tat gat gga agc aat aaa tac tac         180
Glu Trp Val Ala Val Ile Ser Tyr Asp Gly Ser Asn Lys Tyr Tyr
                50                  55                  60 gca gac tcc gtg aag ggc cga ttc acc atc tcc aga gac aat tcc         225
Ala Asp Ser Val Lys Gly Arg Phe Thr Ile Ser Arg Asp Asn Ser
                65                  70                  75 aag aac acg ctg tat ctg caa atg aac agc ctg aga gct gag gac         270
Lys Asn Thr Leu Tyr Leu Gln Met Asn Ser Leu Arg Ala Glu Asp
                80                  85                  90 acg gct gtg tat tac tgt gcg aga gat cgg tta gca gtg gct ggt         315
```

-continued

```
Thr Ala Val Tyr Tyr Cys Ala Arg Asp Arg Leu Ala Val Ala Gly
             95                 100                 105 aga cct ttt gac tac                                          330
Arg Pro Phe Asp Tyr
            110
```